US010195450B2

(12) United States Patent
Delisle

(10) Patent No.: US 10,195,450 B2
(45) Date of Patent: Feb. 5, 2019

(54) ADAPTABLE CLINICAL USAGE PROFILES FOR ADVANCED DEFIBRILLATORS

(71) Applicant: KONINKLIJKE PHILIPS N.V., Eindhoven (NL)

(72) Inventor: Norman Maurice Delisle, Manchester, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/555,090

(22) PCT Filed: Mar. 2, 2016

(86) PCT No.: PCT/IB2016/051143
§ 371 (c)(1),
(2) Date: Sep. 1, 2017

(87) PCT Pub. No.: WO2016/139583
PCT Pub. Date: Sep. 9, 2016

(65) Prior Publication Data
US 2018/0036543 A1 Feb. 8, 2018

Related U.S. Application Data

(60) Provisional application No. 62/127,398, filed on Mar. 3, 2015.

(51) Int. Cl.
*A61N 1/39* (2006.01)
*A61B 5/0205* (2006.01)
(Continued)

(52) U.S. Cl.
CPC ........ *A61N 1/3904* (2017.08); *A61B 5/02055* (2013.01); *A61N 1/3625* (2013.01); *A61N 1/3925* (2013.01); *A61N 1/3993* (2013.01); *A61B 5/024* (2013.01); *A61B 5/0215* (2013.01); *A61B 5/0402* (2013.01); *A61B 5/0816* (2013.01);
(Continued)

(58) Field of Classification Search
None
See application file for complete search history.

(56) References Cited

U.S. PATENT DOCUMENTS 6,405,082 B1 6/2002 Borgenicht
7,805,190 B2 * 9/2010 Chapman ............. A61N 1/3925
607/5
(Continued)

*Primary Examiner* — Brian T Gedeon

(57) ABSTRACT

A controller (20) for an advanced defibrillator (10) employs a therapy manager (30), a monitor manager (40), and a profile manager (50). In operation, the profile manager (50) manages a compilation of clinical usage profiles (60), each clinical usage profile (60) being derived from a different clinical usage of the advanced defibrillator (10) for the patient, and configures the therapy manager (30) and the monitor manager (40) responsive to a selection by a user of the advanced defibrillator (10) of one of the plurality of clinical usage profiles (60). Each clinical usage profile (60) includes a therapy profile (61) specifying a configuration of the therapy manager (30) for a delivery of an electric therapy to the patient. Each clinical usage profile (60) further includes a monitoring profile (62) specifying a configuration of the monitor manager (40) for a measuring of vital parameter(s) of the patient.

20 Claims, 3 Drawing Sheets

(51) Int. Cl.
*A61N 1/362* (2006.01)
*A61B 5/0215* (2006.01)
*A61B 5/024* (2006.01)
*A61B 5/0402* (2006.01)
*A61B 5/08* (2006.01)
*A61B 5/083* (2006.01)
*A61B 5/145* (2006.01)

(52) U.S. Cl.
CPC ......... *A61B 5/0836* (2013.01); *A61B 5/14542* (2013.01)

(56) References Cited

U.S. PATENT DOCUMENTS

| | | |
|---|---|---|
| 8,090,440 B2 | 1/2012 | Chapman et al. |
| 2004/0152954 A1 | 8/2004 | Pearce et al. |
| 2014/0031883 A1 | 1/2014 | Elghazzawi |

\* cited by examiner

ADAPTABLE CLINICAL USAGE PROFILES FOR ADVANCED DEFIBRILLATORS

This application is a national stage application under 35 U.S.C. § 371 of International Application No. PCT/IB2016/051143 filed on Mar. 2, 2016 and published in the English language on Sep. 9, 2016 as International Publication No. WO2016/139583, which claims priority to U.S. Patent Application No. 62/127,398 filed on Mar. 3, 2015, the entire disclosures of which are incorporated herein by reference.

FIELD OF THE INVENTION

The present invention generally relates to defibrillators, including, e.g., advanced life support (ALS) monitor/defibrillators. The present invention specifically relates to adaptable clinical usage profiles for setting a controller of an ALS monitor/defibrillator to a specific clinical situation (e.g., a crash cast usage, an in-hospital transport usage, an electrophysiology lab usage and an emergency medical service usage), a specific clinical usage (e.g. defibrillation, pacing, monitoring), and for a specific patient or clinician.

BACKGROUND OF THE INVENTION

Advanced defibrillator are utilized to provide a variety of patient monitoring and therapy deliveries. More particularly, advanced defibrillators incorporate patient monitoring capabilities including, but not limited to, electrocardiogram ("ECG"), heart rate, pulse rate, pulse oximetry ("SpO2"), exhaled (end tidal) carbon dioxide ("EtCO2"), non-invasive blood pressure ("NIBP"), invasive blood pressure ("IBP"), respiratory rate and temperature. The monitoring capabilities of advanced defibrillators may be displayed in numeric values (e.g., heart rate in beats-per-minute) and/or time-varying waveforms (e.g., ECG waves) and/or alarms (e.g. heart rate too high).

Advanced defibrillators further incorporate electrical therapy delivery capabilities including, but not limited to manual defibrillation, automated external defibrillation ("AED"), synchronized cardioversion, transcutaneous pacing and support for cardiopulmonary resuscitation ("CPR"). The therapy delivery capabilities of advanced defibrillators may be displayed as a selected energy dosage, a delivered energy dosage, a number of delivered shocks or pacing rate and pacing output current.

In the field, this full array of patient monitoring and therapy delivery capabilities is not needed for every clinical situation. In fact, an advanced defibrillator would be more difficult to utilize effectively if all patient monitoring and therapy delivery capabilities were always available simultaneously. For example, the display screen would become cluttered with irrelevant distracting information if control and status information related to pacing were displayed when the device is used to deliver a defibrillation shock. Thus, a current practice for advanced defibrillators is to incorporate modes of operation that make available pre-selected subsets of patient monitoring and therapy delivery capabilities. The following is a description of five (5) typical clinical operation modes.

Manual Defibrillation.

This operation mode is utilized to deliver a defibrillation shock for ventricular fibrillation (i.e. sudden cardiac arrest). In support of the defibrillation shock, key patient parameters being monitored include ECG, SpO2 and EtCO2. Additionally, a control interface enables an energy dose selection and charging of the advanced defibrillator for shocking, and a display illustrates control/status information related to delivering the defibrillation shock including a selected energy dose, a delivered energy dose, and a number of shocks delivered. CPR coaching (e.g. depth and rate of compressions) might also be available be displayed or verbally communicated.

Synchronized Cardioversion.

This operation mode is utilize to deliver a synchronized shock for arrhythmias such as atrial fibrillation. In support of the synchronized shock, key patient parameters being monitored include ECG, SpO2, NIBP and EtCO2. Additionally, a control interface enables an energy dose selection, and the display illustrates control/status information related to delivering the synchronized shock including a selected energy dose, a delivered energy dose, and a number of shocks delivered. CPR coaching information is not needed because the patient is conscious.

Automated External Defibrillation ("AED").

This operation mode is utilized by caregivers with Basic Life Support training (lower skill level than users with Advanced Life support training) to deliver a defibrillation shock, and therefore includes an automatic ECG analysis to determine whether a shock is advised and provides user prompts and graphics to guide the user through the steps of attaching pads, and shocking if needed. Patient monitoring is typically limited to ECG and SpO2 to avoid confusion for the less skilled caregiver. Additionally, the control interface provides for initiating the automatic shock advisory determination and for shocking, and the display illustrates control/status information related to delivering shocks including the delivered energy dose, and the number of shocks delivered is displayed. CPR coaching is also available.

Pacing.

This operation mode is utilized to deliver external pacing pulses for conditions including bradycardia. In support of the pacing pulses, key patient parameters monitored include ECG, SpO2, NIBP and EtCO2. The control interface provides for setting up the pacing, and the display illustrates control/status information related to delivering pace pulses including a pacing rate and a pacing output current, a delivered energy dose and a number of pluses delivered.

Patient Monitoring.

This operation mode is utilized to monitor the patient when electrical therapy delivery is not known to be needed. Includes all monitoring functions. May also include advanced monitoring functions such as diagnostic 12-lead ECG analysis for diagnosis of myocardial infarction (heart attack). Does not provide controls or display information related to therapy delivery, so the entire display screen is available for displaying monitored parameters.

Advanced monitor/defibrillators do not provide capabilities for clinicians or clinical institutions to define other operation modes. However, there are means to customize or adapt the clinical operating modes by pre-configuring various settings related to the appearance of the user interface, how measurements and alarms behave, and how therapy is delivered. For example, high and low alarm limits can be set for heart rate for both adult and pediatric patients, the color of the SpO2 value and its associated pleth wave can be set, and therapy profile such as the default defibrillation shock energy dosage for adults can be set.

Advanced monitor/defibrillators also provide means to modify, during clinical usage, various settings related to therapy delivery, monitoring and the user interface. For example alarm limits can be adjusted for a particular patient, or a monitored parameter (e.g. SpO2) can be enabled or disabled. Additional patient-specific information can also be set during clinical usage including patient demographic data (e.g. name, patient ID, age, gender, etc), whether the patient has an internal pacemaker, etc.

In contrast to the configuration capabilities provided by advanced monitor defibrillators, some advanced patient monitoring devices, such as the Philips IntelliVue Mx800, provide profiles as a more flexible means to adapt the monitor. This profile includes user interface profile and screen layouts, monitoring profile, and monitor settings. Users can select which a profile to use for a particular clinical situation. In effect, instead of providing a limited number of pre-defined monitoring modes, the profile allows the clinician or clinical institution to create clinical monitoring modes adapted to specific patient conditions.

SUMMARY OF THE INVENTION

To improve upon advanced defibrillators, the present invention provides for clinical usage profiles inclusive of therapy profile, monitoring profile, user interface profile and/or device profile associated with a delivery of an electric therapy to a patient and a monitoring of one or more parameters of the patients. The present invention also provides for grouping various combinations of settings from four clinical usage profiles to form custom profiles for a specific patient, a specific clinician, or a specific clinical condition.

The profile unifies the disparate means currently used in advanced monitor/defibrillators to adapt the device to specific clinical situations. The profile replaces the current limited means for providing pre-defined clinical modes of operation, pre-configured settings, and clinical usage settings.

For purposes of the present invention, the term "therapy profile" broadly encompass any setting related to a delivery of a particular electric therapy provided by the advanced defibrillator (e.g., manual defibrillation, synchronized cardioversion, advanced external defibrillation or pacing) including, but not limited to, default patient category (e.g. adult or pediatric), default energy dosage, pace pulse width, default pacing output current and default pacing rate, the term "monitoring profile" broadly encompasses any setting related to measurement of vital parameters and associated alarm parameters including, but not limited to, ECG, ECG bandwidth, heart rate, pulse rate, SpO2, EtCO2, NIBP, IBP, respiratory rate and temperature, the term "user interface profile" broadly encompasses any setting related to the display of the advanced defibrillator including, but not limited to, a display screen, ECG electrode labels, a default voice prompt volume, a default alarm volume, colors for measurements, and default waves measurement sources, and the term "device profile" broadly encompasses any setting related to a general operation of the advanced defibrillator exclusive of the previous settings including, but not limited to, a time and date, printer settings, and mark events.

the term "patient profile" broadly encompasses any setting related to therapy delivery and monitoring of a specific patient inclusive of the previous settings including patient category (e.g. adult or pediatric), patient demographics information (e.g. name, patient ID, age, weight, etc), whether the patient has an internal pacemaker, etc.

the term "clinician profile" broadly encompasses any setting related to therapy delivery and monitoring of a specific patient inclusive of the previous settings including display layout (e.g. font sizes for measurements and waves), and/or clinician information (e.g. name, employee ID, ambulance ID, etc).

the term "clinical condition profile" broadly encompasses any setting related to therapy delivery and monitoring of a specific clinician condition inclusive of the previous settings including available therapies (e.g. pacing or defibrillation), monitored parameters (e.g. which measurements, waves are displayed and which alarms are enabled).

Each new and unique clinical usage profile is implemented for a different clinical usage of the advanced defibrillator including, but not limited to, a clinical environment, the electrical therapies, particulars about the patient and clinician preference.

For purposes of the present invention, the term "clinical environment" encompasses all clinical environments for an advanced defibrillator including, but not limited to, a crash cart, an in-hospital transport, an electrophysiology lab, and an emergency medical service.

For purposes of the present invention, the terms "crash cart", "in-hospital transport", "electrophysiology lab", and "emergency medical service" are to be broadly interpreted as known in the art of the present invention and exemplary described herein.

Generally, monitor/defibrillator usage for crash carts are used in hospitals for emergency cardiac arrest. The monitor/defibrillator is stored on a crash cart (with medications and accessories needed for emergencies). When a patient codes, the crash cart is wheeled to the bedside and shocks are delivered.

Generally, monitor/defibrillator usage for in-hospital transports are used to monitor a patient whose has some risk of cardiac arrest so that a defibrillation shock may be delivered quickly, if needed.

Generally, monitor/defibrillator usage for electrophysiology labs are during defibrillator implantation to resuscitate the patient from induced ventricular fibrillation when testing the implanted device.

Generally, monitor/defibrillator usage for emergency medical service are for a wide variety of patients including those suffering life threatening medical emergencies, as well as significant traumatic injuries. The monitor/defibrillator is carried from the ambulance to the patient where monitoring and therapy delivery functions might be used. Monitoring continues after the patient is stabilized and is transported to the hospital.

One form of the present invention is a controller for an advanced defibrillator employing application modules in the form of a therapy manager, a monitor manager, and a profile manager. In operation, the therapy manager delivers an electric therapy to a patient, and the monitor manager measures vital parameter(s) of the patient.

The profile manager manages a compilation of clinical usage profiles, each clinical usage profile being derived from a different clinical usage of the advanced defibrillator for the patient, and configures the therapy manager and the monitor manager responsive to a selection by a user of the advanced defibrillator of one of the plurality of clinical usage profiles.

Each clinical usage may is based on a clinical environment, an electric therapy, a patient information (e.g., age, cardiovascular condition, respiratory condition, etc.), a user preference, and/or any over factor related to the use of the advanced defibrillator in a clinical situation.

Each clinical usage profile (60) includes a therapy profile (61) specifying a configuration of the therapy manager (30) for a delivery of an electric therapy to the patient.

Each clinical usage profile (60) further includes a monitoring profile (62) specifying a configuration of the monitor manager (40) for a measuring of vital parameter(s) of the patient.

For purposes of the present invention, the term "controller" broadly encompasses all structural configurations of an application specific main board or an application specific integrated circuit housed within or linked to a medical device for controlling an application of various inventive principles of the present invention as subsequently described herein. The structural configuration of the controller may include, but is not limited to, processor(s), computer-usable/computer readable storage medium(s), an operating system, application module(s), peripheral device controller(s), slot(s) and port(s).

For purposes of the present invention, the term "application module" broadly encompasses an electronic circuit or an executable program (e.g., executable software and/firmware) for executing a specific application.

For purposes of the present invention, the term "clinical usage profile" broadly encompasses a therapy profile, a monitoring profile, an optional user interface profile, an optional device therapy and any addition data contained within a data structure including, but not limited to, a computer data file and a computer database.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

To facilitate an understanding of the present invention, exemplary embodiments of the present invention will be provided herein directed to a controller 20 (FIG. 2) of a defibrillator 10 (FIG. 1) in the form of a commercially available HeartStart MRx Monitor/Defibrillator, for example. From description of the exemplary embodiments as shown in FIGS. 1-5, those having ordinary skill in the art will appreciate how to make and use the present invention for implementation by/integration into any defibrillator known in the art prior to or subsequent to the present invention (e.g., any ALS monitor/defibrillator and any AED).

Figure 1A:
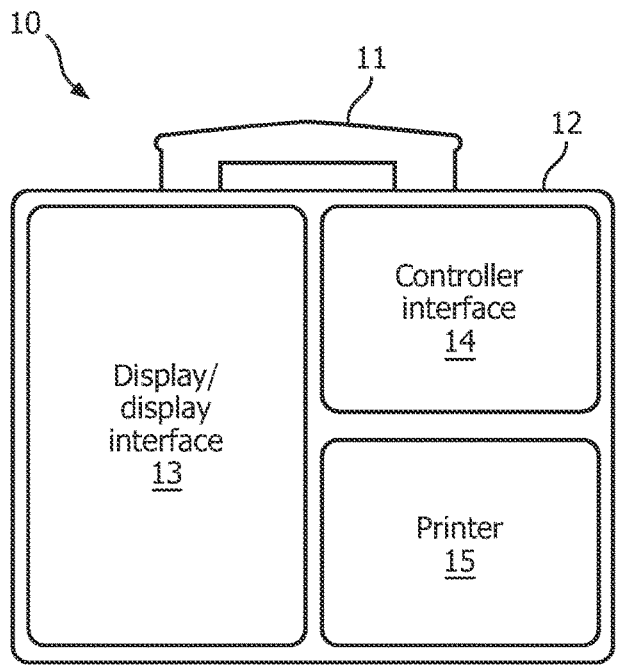
FIGS. 1A and 1B respectively illustrate a front view and a side view of an exemplary portable monitor/defibrillator in accordance with the inventive principles of the present invention.
Figure 1B:
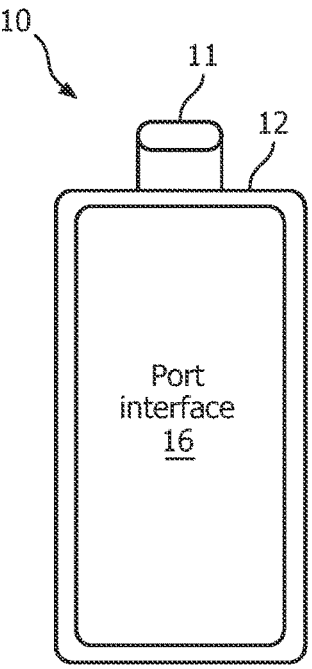
Figure 2:
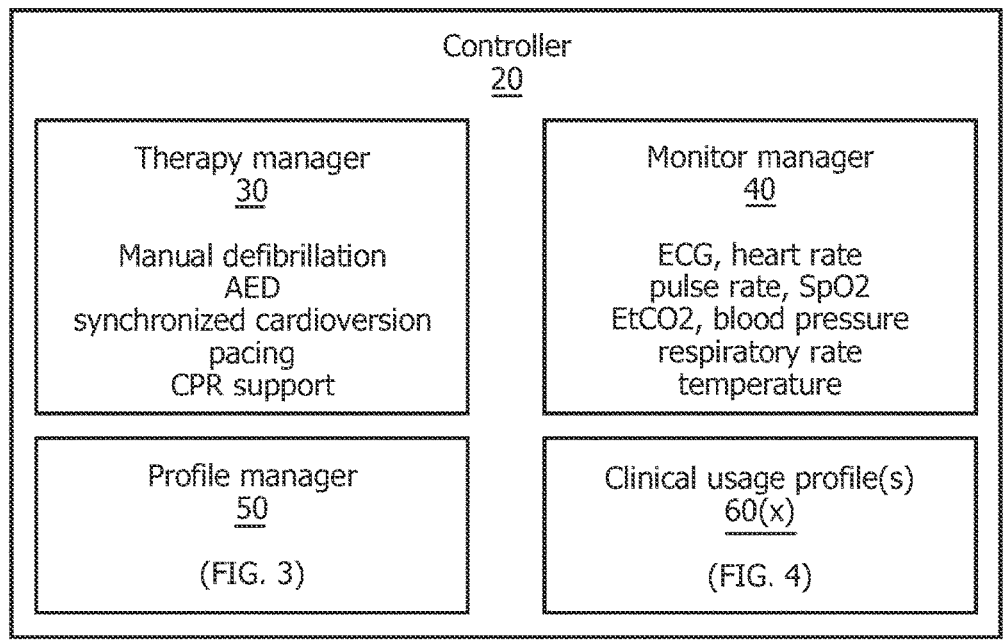
FIG. 2 illustrates a block diagram of an exemplary controller in accordance with the inventive principles of the present invention.

Referring to FIGS. 1 and 2, a block diagram of defibrillator 10 shows a handle 11 attached to a housing 12 providing user-access to a display/display interface 13, a controller interface 14, a printer 15 and a port interface 16 as shown in FIG. 1. Housing 12 further encloses controller 20 as shown in FIG. 2.

As known in the art:

(1) display/display interface 13 displays patient monitoring data (e.g., ECG data) as customized by a user via a display interface 13 (e.g., keys);

(2) controller interface 14 (e.g., knobs and buttons) allows the user to apply various electric therapies (e.g., shocks, cardioversion, pacing, etc.) to a patient as controlled by controller 20;

(3) printer 15 allows the user to print various patient reports, status logs and device information;

(4) port interface 16 allows for the connection by the user of one or more patient monitoring sensors to controller 20 including, but not limited to, a blood pressure sensor, a blood oxygen sensor and a carbon dioxide sensor (not shown);

(5) controller 20 includes a therapy manager 30 to execute various algorithms for delivering an electrical therapy to the patient including, but not limited to, manual defibrillation, synchronized cardioversion, advanced external defibrillation and pacing; and (6) controller 20 further includes a monitor manager 40 to execute various algorithms for measuring vital parameters of a patient including, but not limited to, ECG, heart rate, pulse rate, SpO2, EtCO2, NIBP, IBP, respiratory rate and temperature.

By the inventive principles of the present invention, controller 20 further includes a profile manager 50 to implement one of an X number of clinical usage profiles 60, X≥1, for adapting therapy manager 30 and monitor manager 40 to a specific clinical usage including, but not limited to, a clinical environment, an electric therapy, patient information and user preference.

Figure 3:
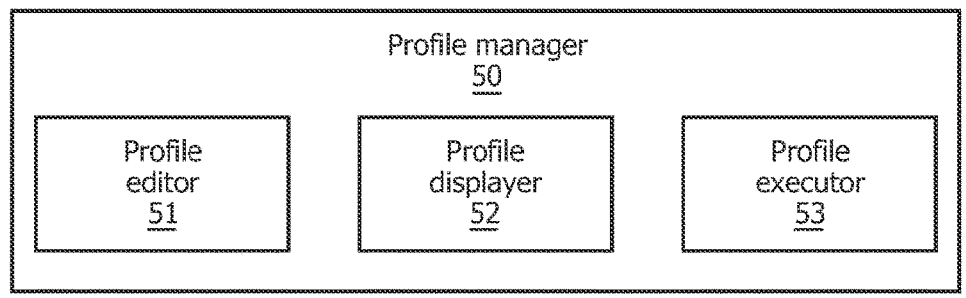
FIG. 3 illustrates a block diagram of an exemplary profile manager in accordance with the inventive principles of the present invention.

In practice as shown in FIG. 3, profile manager 50 may employ a profile editor 51 for generating/editing each clinical usage profile 60, a profile displayer 52 for displaying information/icon of each clinical usage profile 60 for selection by a user of defibrillator 10, and a profile executor 53 for executing a selected clinical usage profile 60 in configuring therapy manager 30 and monitor manager 40. For purposes of the present invention, the terms "generating", "editing", "displaying" and "executing" of a clinical usage profile 60 are to be broadly interpreted as known in the art of the present invention and exemplary described herein.

In practice, each clinical usage profile 60 may be generated during a manufacturing of defibrillator 10 or by defibrillator 10.

Figure 4:
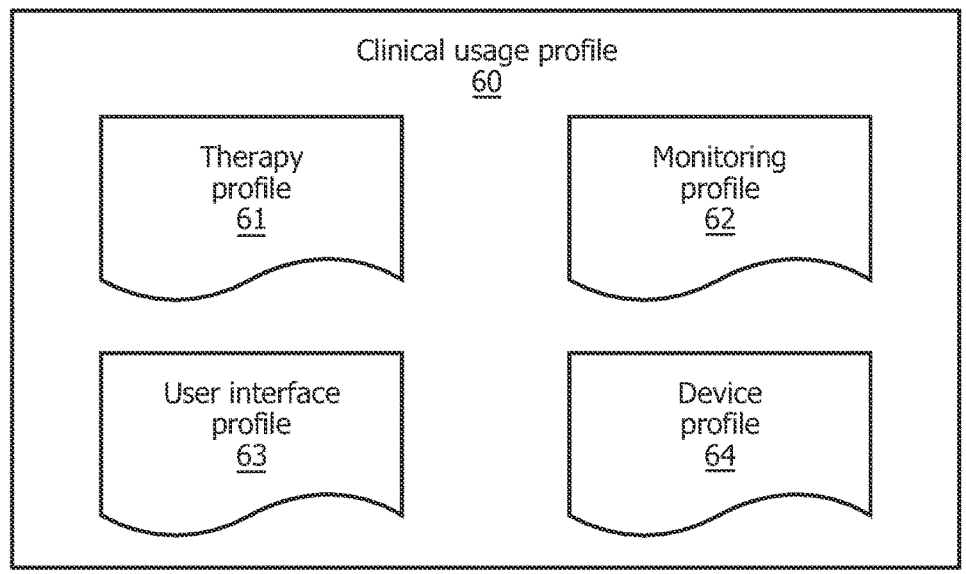
FIG. 4 illustrates a block diagram of an exemplary clinical usage profile in accordance with the inventive principles of the present invention.

In practice as shown in FIG. 4, each clinical usage profile 60 includes therapy profile 61, monitoring profile 62, user interface profile 63, device profile 64 and any additional data corresponding to the specific clinical usage. In one embodiment, the settings data/additional data are contained within a computer file and formatted in accordance with a standard or proprietary format (e.g., Extensible Markup Language "XML"). In an alternative embodiment, the settings/additional data may be structured for any type of database/repository (e.g., a document oriented database or an XML database).

Figure 5:
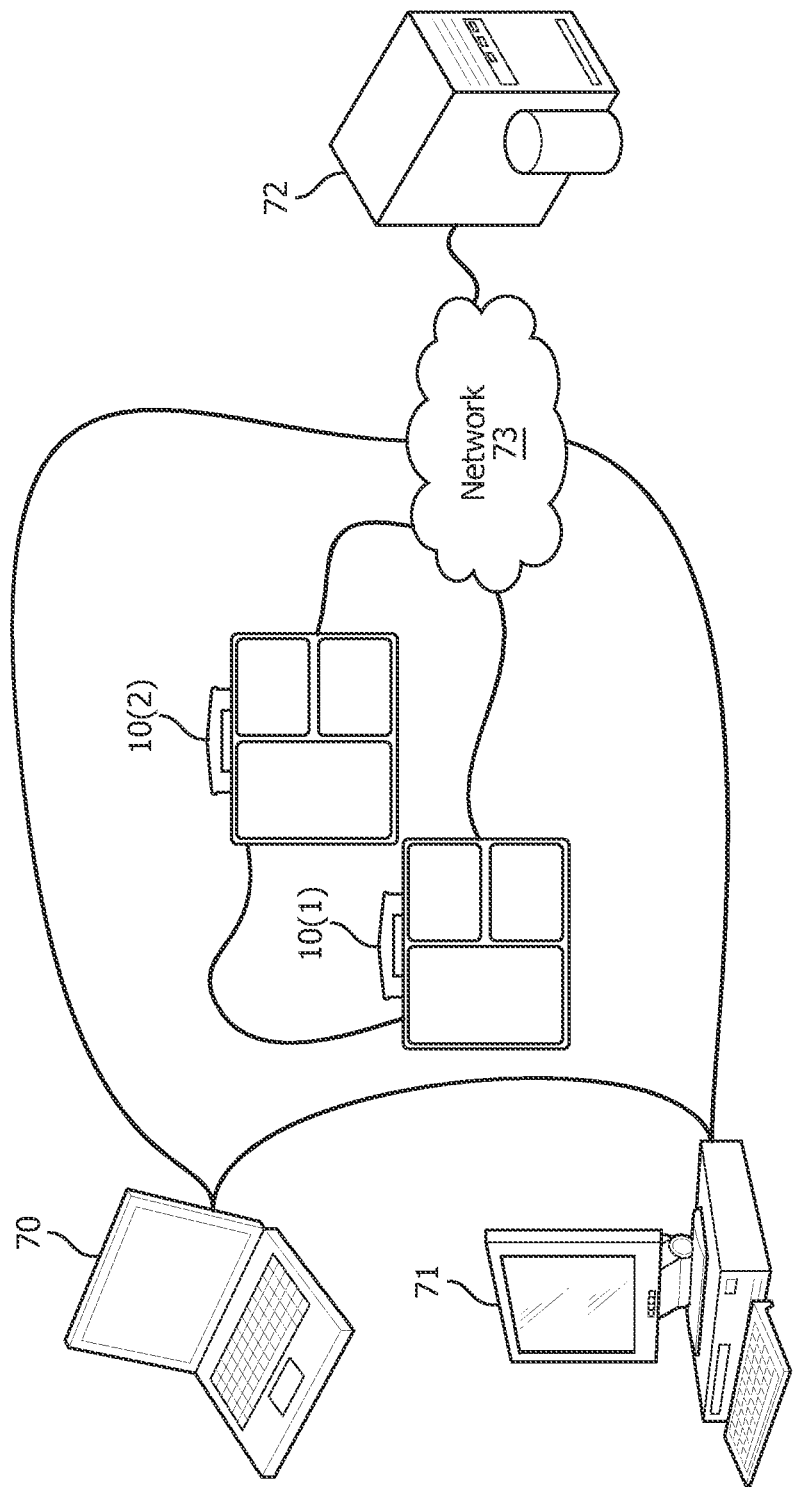
FIG. 5 illustrates a schematic diagram of an exemplary loading of clinical usage profiles to a portable monitor/defibrillator of FIG. 1 in accordance with the inventive principles of the present invention.

In practice as shown in FIG. 5, profile editor 51 and/or profile displayer 52 may concurrently or alternatively be installed on a computing device including, but not limited to, a laptop 70, a workstation 71 and a server 72 whereby a clinical usage profile 60 may be generated and/or edited remotely either via a direct wired or wireless connection to a defibrillator 10. Network 73 may be any type of network utilized in the art of the present invention.

Moreover, one or more of the clinical usage profiles 60 may be exported from or imported to defibrillator 10a, and may be exchanged between defibrillator 10a with another device, particularly another defibrillator 10b, a patient monitoring device or another medical device that uses some or all of the settings in a monitor/defibrillator's clinical usage profile. For purposes of the present invention, the terms "export", "import" and "exchange" of a clinical usage profile 60 are to be broadly interpreted as known in the art of the present invention and exemplary described herein. The exporting/importing/exchange capability of defibrillator 10 provides numerous advantages. For example, if a patient is being monitored by a bedside patient monitor, the clinical usage profile 60 could be transmitted to a defibrillator that is wheeled into the room on a crash cart. Those skilled in the art will appreciate numerous additional examples.

To further describe the inventive principles of the present invention, the following are examples of clinical usage profiles of the present invention as applied to commercially available defibrillator/monitor devices (e.g., Philips XL+ and HeartStart MRx). From these examples, one having ordinary skill is the art will appreciate in view of the preset disclosure that various and numerous additional clinical usage scenarios for each of mode of operation of a defibrillator.

Generally, via a selection of a particular clinical usage profile 60 (FIG. 4) (e.g., by display interface 13 and/or controller interface 14), profile executor 53 (FIG. 3) executes a pre-configuration of settings in accordance with the selected clinical usage profile.

Mode 1: Patient Monitoring.

This mode is applicable to all clinical situations involving a monitoring the patient before or after therapy application and may include the following measurement/user interface profile:
  1. Patient category: pre-set to adult or infant/child depending on most frequent usage;
  2. Alarms settings (e.g. tone, volume);
  3. Colors of measurements and waveforms for consistency with other medical devices and easy recognition;
  4. Alarm Limits (e.g. high & low limits for Heart Rate, SpO2, Pulse Rate, etc.); and
  5. ECG wave defaults (which ECG lead is displayed in each display sector).

Mode 2: Manual Defibrillation:

This mode is applicable to all clinical situations involving manual defibrillation of the patient and typically includes the following steps for delivering a shock:
  1. The knob is turned to the desired energy. For example, 150 J is the standard adult dose;
  2. The Patient Category setting is adult (the default, so the user does not need to push the button, the adult category is displayed);
  3. The device will present an alarm for ventricular fibrillation ("VFIB");
  4. An ECG wave is displayed—it is acquired either via the pads or paddles being used to deliver the shock, of via an ECG leadset with electrodes places on the patient's chest. The ECG Lead select button can be pushed to select which ECG leads to view. In an urgent situation like cardiac arrest, the default ECG acquired via the pads or paddles is used.
  5. The charge button is pressed. There is a charging tone and then a charged tone after a few seconds. The display indicated the device is charged and the shock button is flashing.
  6. The shock button is pressed to deliver the shock.
  7. Steps 4 and 5 are repeated if the patient if the sinus rhythm is not restored. CPR might be performed before each shock, but there are no device therapy to allow CPR.

This mode may also be impacted by the following therapy profile:
  1. Default low-energy setting (from 1 to 10 J); and
  2. Time to auto-disarm (if device gets charged but shock is not delivered).

Mode 3:

Synchronized Cardioversion. This mode is applicable to all clinical situations involving synchronized cardioversion of the patient and includes steps similar to manual defibrillation, except the defibrillator is placed in "sync" mode and the ECG wave is diagnosis to ensure the defibrillator is set up properly to detect the R-Wave. More particularly, the steps of this mode include:
  1. The knob is turned to the desired energy. For example, 150 J is the standard adult dose;
  2. The Patient Category setting is adult (the default, so the user does not need to push the button, the adult category is displayed);
  3. The "sync" button is pressed—it illuminates indicating sync mode, and there is a sync indicator displayed on the screen;
  4. The device can be used to check blood pressure. To do so, a button is pressed to initiate cuff inflation;
  5. The device can be used to check SpO2. No device buttons need to be pushed;
  6. An ECG wave is displayed with R-wave markers—for cardioversion an ECG leadset is used. R-wave markers are displayed on the ECG wave. The ECG Lead select button is pushed to select an ECG lead where the R-wave markers are prominent and properly detected;
  7. The charge button is pressed. There is a charging tone and then a charged tone after a few seconds. The display indicated the device is charged and the shock button is flashing;
  8. The shock button is held down until the shock is delivered (a second or so); and
  9. Steps 4, 5 and 6 are repeated if the patient if the normal sinus rhythm is not restored.

This mode may include the following therapy profile:
  1. All pre-configured settings for Manual Defibrillation
  2. Whether device remains in sync mode after shock Mode 4: AED Defibrillation.

This mode is applicable to all clinical situations involving AED of the patient and typically includes the following steps for delivering a shock:
  1. The knob is turned to AED mode.
  2. The Patient Category setting is adult by default, so it is pressed it he patient is infant or child. The patient category is announced via voice prompt when AED mode is entered and when the user changes patient category.

3. The device prompts the user to connect pads using voice prompts and displayed prompts messages.
4. Once the device detects that pads are connected, it automatically analyzes the ECG signal to determine whether a shock should be given.
5. If shock is advised, the device automatically changes to the default energy appropriate for the patient category. There is a charging tone and then a charged tone after a few seconds. The display indicated the device is charged and the shock button is flashing and a voice prompt says to press the shock button.
6. The shock button is pressed to deliver the shock.
7. The device prompts the user to preform CPR.
8. After 2 minutes of CPR, the device prompts the user to stop CPR and steps 4 thru 7 are repeated until a shock is not advised.

This mode may include the following therapy profile:
1. All pre-configured settings for manual defibrillation;
2. Whether energy is escalated after each shock (e.g. 150 J, 170 J, 200 J);
3. Amount of detail in voice prompts;
4. Whether SpO2 monitoring is performed in AED mode;
5. What action to take if no shock is advised (e.g. perform CPR, monitor patient); and
6. CPR time interval (e.g. 2 mins).

Mode 5: Pacing.

This mode is applicable to all clinical situations involving pacing of the patient and typically includes the following steps for delivering a shock:
1. The knob is turned to Pacing Mode. By default the device enters "demand pacing" mode. The user can push a button to change to "fixed pacing". Demand pacing is preferred because pace pulses are only delivered when needed—no pace pulse is delivered when the user's intrinsic rhythm produces an R-wave;
2. The Patient Category setting is adult (the default, so the user does not need to push the button, the adult category is displayed);
3. The device can be used to check blood pressure. To do so, a button is pressed to initiate cuff inflation;
4. The device can be used to check SpO2. No device buttons need to be pushed;
5. The heart rate is displayed—the device will present an alarm for extreme bradycardia;
6. An ECG wave is displayed with R-wave markers (in demand pacing mode)—for demand pacing an ECG leadset is used. R-wave markers are displayed on the ECG wave. The ECG Lead select button is pushed to select an ECG lead where the R-wave markers are correctly detected;
7. A button is pressed to start pacing;
8. Up/down buttons are pressed to set the desired pacing rate (e.g. 80 bpm); and
9. Up/down buttons are pressed to set the pacing output current and achieve capture (the ECG wave shows when the device output level is sufficient to pace the heart).

This mode may include the following therapy profile:
1. Default pacing rate and output current; and
2. Pace pulse width (20 or 40 msecs)

From the description of FIGS. 1-5 and the examples, those having ordinary skill in the art will appreciate the various benefits of the present invention including, but not limited to, an expansion of existing clinical mode switching of defibrillators to profile controlled defibrillators having numerous additional modes.

For example, the clinical usage profiles may be generally applicable and be labelled as follows:
1. a crash cart;
2. an in-hospital transport;
3. an electrophysiology lab; and
4. an emergency medical service.

By even further example, the clinical usage profile may be electric therapy specific and be labelled as follows:
1. a manual defibrillation crash cart;
2. a manual defibrillation in-hospital transport;
3. an advanced external defibrillation electrophysiology lab;
4. an advanced external defibrillation emergency medical service;
5. a synchronized cardioversion crash cart;
6. a synchronized cardioversion in-hospital transport;
7. a pacing electrophysiology lab; and
8. a pacing emergency medical service.

By even further example, the clinical usage profile may be age specific and be labelled as follows:
1. a pediatric crash cart;
2. a pediatric in-hospital transport;
3. a pediatric electrophysiology lab;
4. a pediatric emergency medical service;
5. an adult crash cart;
6. an adult in-hospital transport;
7. an adult electrophysiology lab; and
8. an adult emergency medical service.

By even further example, the clinical usage profile may be health specific to the patient in terms of the number of previous shocks and be labelled as follows:
1. a low health risk pediatric crash cart;
2. a low health risk pediatric in-hospital transport;
3. a low health risk electrophysiology lab;
4. a low health risk emergency medical service;
5. a high health risk crash cart;
6. a high health risk in-hospital transport;
7. a high health risk electrophysiology lab; and
8. a high health risk emergency medical service.

Additional examples may be related to alarm limits for a particular patient, a disabling of particular measurement of vital parameter(s) as well as other factors as would be appreciated by those having ordinary skill in the art.

In summary, as one having ordinary skill in the art will appreciate in view of the teachings provided herein, features, elements, components, etc. described in the present disclosure/specification and/or depicted in the FIGS. 1-5 may be implemented in various combinations of electronic components/circuitry, hardware, executable software and executable firmware, particularly of a controller as described herein, and provide functions which may be combined in a single element or multiple elements. For example, the functions of the various features, elements, components, etc. shown/illustrated/depicted in the FIGS. 1-5 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive system and method for controlling an advanced defibrillator via clinical usage profiles, (which embodiments are intended to be illustrative and not limiting), it is noted that modifications and variations can be made by persons having ordinary skill in the art in light of the teachings provided herein, including the FIGS. 1-5. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A controller for an advanced defibrillator, the controller comprising:
   a therapy manager operable to manage a delivery of a plurality of electric therapies to a patient;
   a monitor manager operable to manage a measuring of vital parameters of the patient; and
   a profile manager operable to manage a compilation of clinical usage profiles, each clinical usage profile being derived from a different clinical usage of the advanced defibrillator for the patient,
      wherein each clinical usage profile includes a therapy profile specifying a configuration of the therapy manager for a delivery of one of the electric therapies to the patient,
      wherein each clinical usage profile further includes a monitoring profile specifying a configuration of the monitor manager for a measuring of at least one of the vital parameters of the patient,
      wherein the profile manager is configured to configure the therapy manager and the monitor manager responsive to a selection by a user of the advanced defibrillator of one of the plurality of clinical usage profiles, and
   wherein each clinical usage profile is based on one of a plurality of clinical environments including a crash cart, an in-hospital transport, an electrophysiology lab and an emergency medical service.

2. The controller of claim 1, wherein each clinical usage profile is based on one of the electrical therapies including a manual defibrillation, a synchronized cardioversion, an advanced external defibrillation and a pacing.

3. The controller of claim of claim 1, wherein each clinical usage profile is based on at least one of an age of the patient, a cardiovascular condition of the patient or a respiratory condition of the patient.

4. The controller of claim of claim 1, wherein each clinical usage profile is based on a user preference of the therapy manager and the monitor manager.

5. The controller of claim 1, wherein each therapy profile includes a delivery setting of at least one of a default patient category, a default energy dosage, a pace pulse width, a default pacing output current or a default pacing rate.

6. The controller of claim 1, wherein each monitor profile includes a measurement setting of at least one of an ECG, an FCG bandwidth, a heart rate, a pulse rate, SpO2, EtCO2, NIBP, IBP, a respiratory rate or a temperature.

7. The controller of claim 1, wherein each clinical usage profile further includes a user interface profile specifying a display operation of the advanced defibrillator.

8. The controller of claim 7, wherein each user interface profile includes a display setting of at least one of a display screen layout, ECG electrode labels, a default voice prompt volume, a default alarm volume, colors for measurements or default waves measurement sources.

9. The controller of claim 1, wherein each clinical usage profile further includes a device profile specifying a general operation of the advanced defibrillator.

10. The controller of claim 1, wherein the profile manager is further operable to at least one of generate or edit each clinical usage profile.

11. The controller of claim 10, wherein each device profile includes an operational setting of at least one of a time and date, a printer or mark events.

12. The controller of claim 1, wherein the profile manager is further operable to export at least a portion of at least one of the clinical usage profiles to another device.

13. The controller of claim 1, wherein the profile manager is further operable to import at least a portion of at least one clinical usage profile from another device.

14. The controller of claim 1, wherein the profile manager is further operable to exchange at least one clinical usage profile with another device.

15. The controller of claim 1, wherein at least one clinical usage profile of the compilation of clinical usage profiles is based on a clinical environment of the plurality of clinical environments that is a crash cart.

16. The controller of claim 1, wherein at least one clinical usage profile of the compilation of clinical usage profiles is based on a clinical environment of the plurality of clinical environments that is an in-hospital transport.

17. The controller of claim 1, wherein at least one clinical usage profile of the compilation of clinical usage profiles is based on a clinical environment of the plurality of clinical environments that is an electrophysiology lab.

18. The controller of claim 1, wherein at least one clinical usage profile of the compilation of clinical usage profiles is based on a clinical environment of the plurality of clinical environments that is an emergency medical service.

19. A method of operating a controller for an advanced defibrillator, the controller including a therapy manager, a monitor manager and a profile manager, the method comprising:

the profile manager managing a compilation of clinical usage profiles, each clinical usage profile being derived from a different clinical usage of the advanced defibrillator for the patient, wherein each clinical usage profile includes a therapy profile specifying a configuration of the therapy manager for a delivery of an electric therapy to the patient, and wherein each clinical usage profile further includes a monitoring profile specifying a configuration of the monitor manager for a measuring of at least one vital parameter of the patient; and the profile manager configuring the therapy manager and the monitor manager responsive to a selection by a user of the advanced defibrillator of one of the plurality of clinical usage profiles; and wherein each clinical usage profile is based on one of a plurality of clinical environments including a crash cart, an in-hospital transport, an electrophysiology lab and an emergency medical service.

20. A defibrillator, comprising:

one or more processors programmed to:

measure vital parameters of the patient; and manage a compilation of clinical usage profiles, each clinical usage profile being derived from a different clinical usage of the defibrillator for the patient;

wherein each clinical usage profile includes a monitoring profile specifying a configuration of a monitor manager for measuring of at least one of the vital parameters of the patient;

wherein each clinical usage profile is based on one of a plurality of clinical environments including a crash cart, an in-hospital transport, an electrophysiology lab and an emergency medical service; and wherein the defibrillator is configured to deliver electric therapy based on input received through a clinical usage profile of the compilation of clinical usage profiles.

* * * * *